US00PP18362P2

(12) United States Plant Patent
McGaughey

(10) Patent No.: US PP18,362 P2
(45) Date of Patent: Dec. 25, 2007

(54) ***CHRYSANTHEMUM* PLANT NAMED 'DARK BRONZE CHERIE'**

(50) Latin Name: *Chrysanthemum×morifolium*
Varietal Denomination: Dark Bronze Cherie

(75) Inventor: Annette N. McGaughey, Branford (CA)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/472,750

(22) Filed: Jun. 22, 2006

(51) Int. Cl.
*A01H 5/00* (2006.01)

(52) U.S. Cl. ..... Plt./296

(58) Field of Classification Search ..... Plt./296
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Dark Bronze Cherie', characterized by its compact, upright, spreading and uniformly mounded plant habit; freely branching and moderately vigorous growth habit; small dark green-colored foliage; uniform and early flowering habit; freely flowering habit; small daisy-type inflorescences with dark bronze-colored ray florets; and good postproduction longevity.

2 Drawing Sheets

Botanical description: *Chrysanthemum×morifolium.*
Cultivar denomination: 'Dark Bronze Cherie'.

BACKGROUND OF THE INVENTION

The present invention relates to a new and distinct cultivar of *Chrysanthemum* plant, botanically known as *Chrysanthemum×morifolium,* commercially grown as a potted *Chrysanthemum* and hereinafter referred to by the name 'Dark Bronze Cherie'.

The new *Chrysanthemum* is a naturally-occurring whole plant mutation of the *Chrysanthemum×morifolium* cultivar Apricot Cherie, disclosed in U.S. Plant Pat. No. 12,961. The new *Chrysanthemum* was discovered and selected by the Inventor as a single flowering plant within a population of plants of the cultivar Apricot Cherie in February, 2003 in Brantford, Ontario, Canada. The selection of this plant was based on its unique ray floret coloration.

Asexual reproduction of the new *Chrysanthemum* by vegetative tip cuttings was first conducted in Brantford, Ontario, Canada in May, 2003. Asexual reproduction by cuttings has shown that the unique features of the new *Chrysanthemum* are stable and reproduced true to type in successive generations.

SUMMARY OF THE INVENTION

Plants of the cultivar Dark Bronze Cherie have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dark Bronze Cherie'. These characteristics in combination distinguish 'Dark Bronze Cherie' as a new and distinct potted *Chrysanthemum* cultivar:

1. Compact, upright, spreading and uniformly mounded plant habit.
2. Freely branching and moderately vigorous growth habit.
3. Small dark green-colored foliage.
4. Uniform flowering response.
5. Typically grown as a center-budded or as natural spray type.
6. Early flowering habit, eight-week response time.
7. Freely flowering habit.
8. Small daisy-type inflorescences with dark bronze-colored ray florets.
9. Good postproduction longevity with plants maintaining good substance and color for about three weeks in an interior environment.

Plants of the new *Chrysanthemum* differ from plants of the parent, the cultivar Apricot Cherie primarily in ray floret color as plants of the cultivar Apricot Cherie have apricot pink-colored ray florets.

Plants of the new *Chrysanthemum* can be compared to plants of the *Chrysanthemum* cultivar Bronze Cherie, disclosed in U.S. Plant Pat. No. 9,702. In side-by-side comparisons conducted in Fort Myers, Fla., plants of the new *Chrysanthemum* differed from plants of the cultivar Bronze Cherie primarily in ray floret color as plants of the new *Chrysanthemum* had darker bronze-colored ray florets than plants of the cultivar Bronze Cherie.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plants of 'Dark Bronze Cherie'.

The photograph on the second sheet is a close-up view of typical inflorescences of 'Dark Bronze Cherie'.

DETAILED BOTANICAL DESCRIPTION

The aforementioned photographs and following observations and measurements describe plants grown during the spring in Leamington, Ontario, Canada during the spring in a polycarbonate-covered greenhouse and under conditions and practices which approximate those generally used in commercial potted *Chrysanthemum* production. During the production of the plants, day temperatures averaged 22.5° C., night temperatures averaged 18° C. and light levels ranged from 4,000 to 6,000 foot candles. Four unrooted cuttings were directly stuck in 15-containers, exposed to long day/short night conditions, and pinched about two weeks later. At that time, the photoinductive short day/long night treatments were started. Plants used in the photographs and for the description were grown as natural spray types and were about two months old. In the following description, color references are made to The Royal Horticultural Society Colour Chart, 1995 Edition, except where general terms of ordinary dictionary significance are used.

Botanical classification: *Chrysanthemum×morifolium* cultivar Dark Bronze Cherie.

Parentage: Naturally-occurring whole plant mutation of the *Chrysanthemum×morifolium* cultivar Apricot Cherie, disclosed in U.S. Plant Pat. No. 12,961.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Fine to thick, fibrous; white in color.

*Rooting habit.*—Freely branching; moderately dense.

Plant description:

*Appearance.*—Herbaceous daisy-type potted *Chrysanthemum* typically grown as a center-budded or as a natural spray type. Stems upright and outwardly spreading giving a uniformly mounded appearance to the plant. Freely branching habit, about five or six lateral branches develop after removal of terminal apex (pinching); dense and full plant habit. Compact and moderately vigorous growth habit.

*Plant height.*—About 20 cm.

*Plant width.*—About 41 cm.

*Lateral branches.*—Length: About 17 cm. Diameter: About 3.5 mm. Internode length: About 1.7 cm. Strength: Strong. Texture: Pubescent. Color: Darker than 144A to 146A.

Foliage description:

*Arrangement.*—Alternate, simple.

*Length.*—About 4.7 cm.

*Width.*—About 3.5 cm.

*Apex.*—Cuspidate to mucronate.

*Base.*—Attenuate with truncate tendencies.

*Margin.*—Palmately lobed, sinuses between lateral lobes parallel to divergent.

*Texture, upper and lower surfaces.*—Fine pubescence; veins prominent on lower surface.

*Color.*—Developing and fully developed foliage, upper surface: Darker and more green than 147A; venation, close to 147A. Developing and fully developed foliage, lower surface: Close to 147B; close to 147B.

*Petiole length.*—About 2.3 cm.

*Petiole diameter.*—About 3 mm.

*Petiole color.*—Close to 146A to 146B.

Inflorescence description:

*Appearance.*—Daisy-type inflorescence form with elongated oblong-shaped ray florets. Inflorescences borne on terminals above foliage. Disk and ray florets arranged acropetally on a capitulum. Inflorescence not fragrant. Typically grown as a center-budded or as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to two weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—Freely flowering, about 18 inflorescences develop per lateral stem, or about 90 to 108 inflorescences per plant.

*Inflorescence bud.*—Height: About 4 mm. Diameter: About 5 mm. Shape: Oblate. Color: Close to 146A to 147A.

*Inflorescence size.*—Diameter: About 3.8 cm. Depth (height): About 1.3 cm. Diameter of disc: About 1.2 cm. Receptacle diameter: About 4 mm.

*Ray florets.*—Shape: Elongated-oblong. Orientation: Initially upright, then about 75° from vertical. Aspect: Initially incurved, then mostly flat. Length: About 1.7 cm. Width: About 5 mm. Corolla tube length: About 2.5 mm. Apex: Acute, rounded or emarginate. Base: Attenuate; short corolla tube. Margin: Entire. Texture, upper and lower surfaces: Smooth, glabrous, satiny. Number of ray florets per inflorescence: About 26 arranged in one or two rows. Color: When opening to fully opened, upper surface: Close to 6A overlain with close to 45A; with development, more faintly overlain with close to 45A. When opening to fully opened, lower surface: Close to 6C underlain with close to 46A; with development, more faintly underlain with 46A.

*Disc florets.*—Arrangement: Massed at center of receptacle. Shape: Tubular, elongated. Apex: Five-pointed. Length: About 5 mm. Width: Apex: About 2 mm. Base: About 1 mm. Number of disc florets per inflorescence: About 105. Color: Immature: Close to 154A. Mature: Apex: Close to 9A. Mid-section: Close to 145D. Base: Close to 155D.

*Phyllaries.*—Number of phyllaries per inflorescence: About 20. Length: About 5.5 mm. Width: About 2 mm. Shape: Linear. Apex: Acute. Base: Truncate. Texture, upper surface: Smooth, waxy. Texture, lower surface: Pubescent. Color, upper surface: Close to 146A. Color, lower surface: Close to 146A to 147A.

*Peduncles.*—Length: First peduncle: About 3.2 cm. Fourth peduncle: About 3.8 cm. Seventh peduncle:

About 6.5 cm. Diameter (first peduncle): About 2 mm. Angle: About 40° from vertical. Strength: Strong, flexible. Texture: Pubescent. Color: Close to 144A to 146A.

*Reproductive organs.*—Androecium: Present on disc florets only. Filament length: About 5 mm. Filament color: Close to 155D. Anther shape: Oblong. Anther color: 12A. Pollen amount: None observed. Gynoecium: Present on both ray and disc florets. Pistil length: About 4.5 mm. Stigma shape: Bi-parted. Stigma color: Close to 12A. Style length: About 3.5 mm. Style color: Close to 145D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 1° C. and high temperatures of about 38° C.

It is claimed:

1. A new and distinct *Chrysanthemum* plant named 'Dark Bronze Cherie' as illustrated and described.

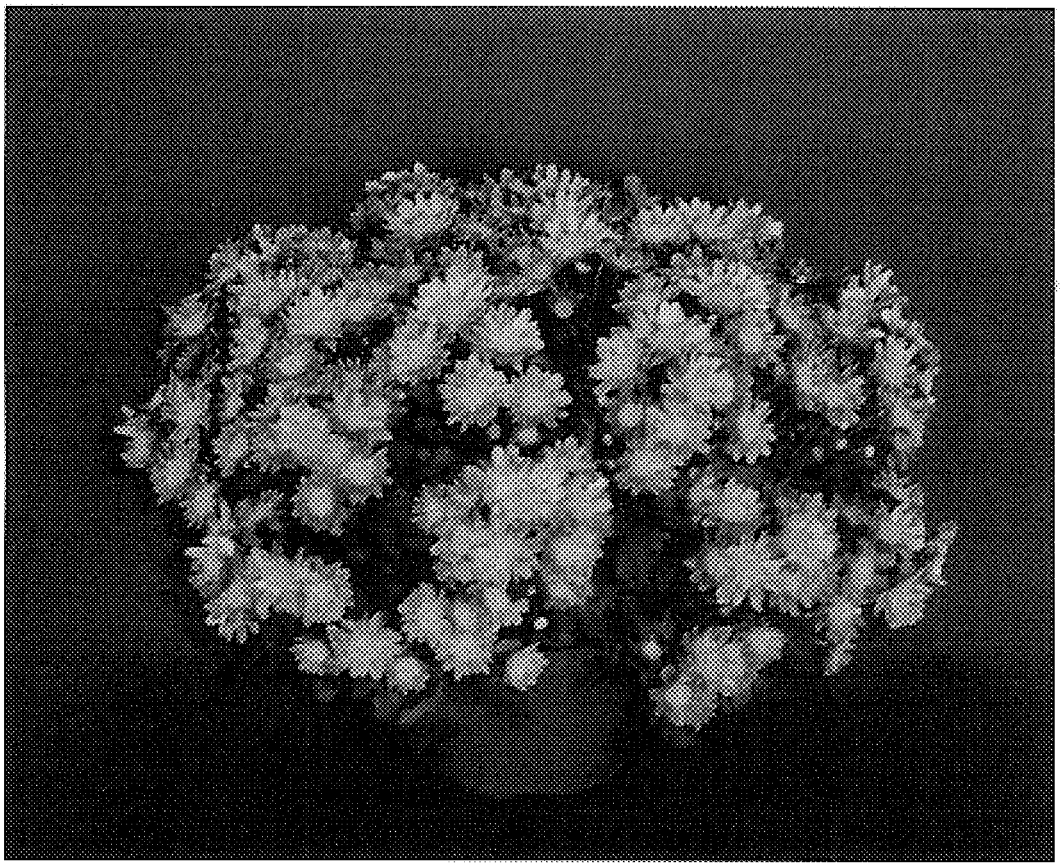

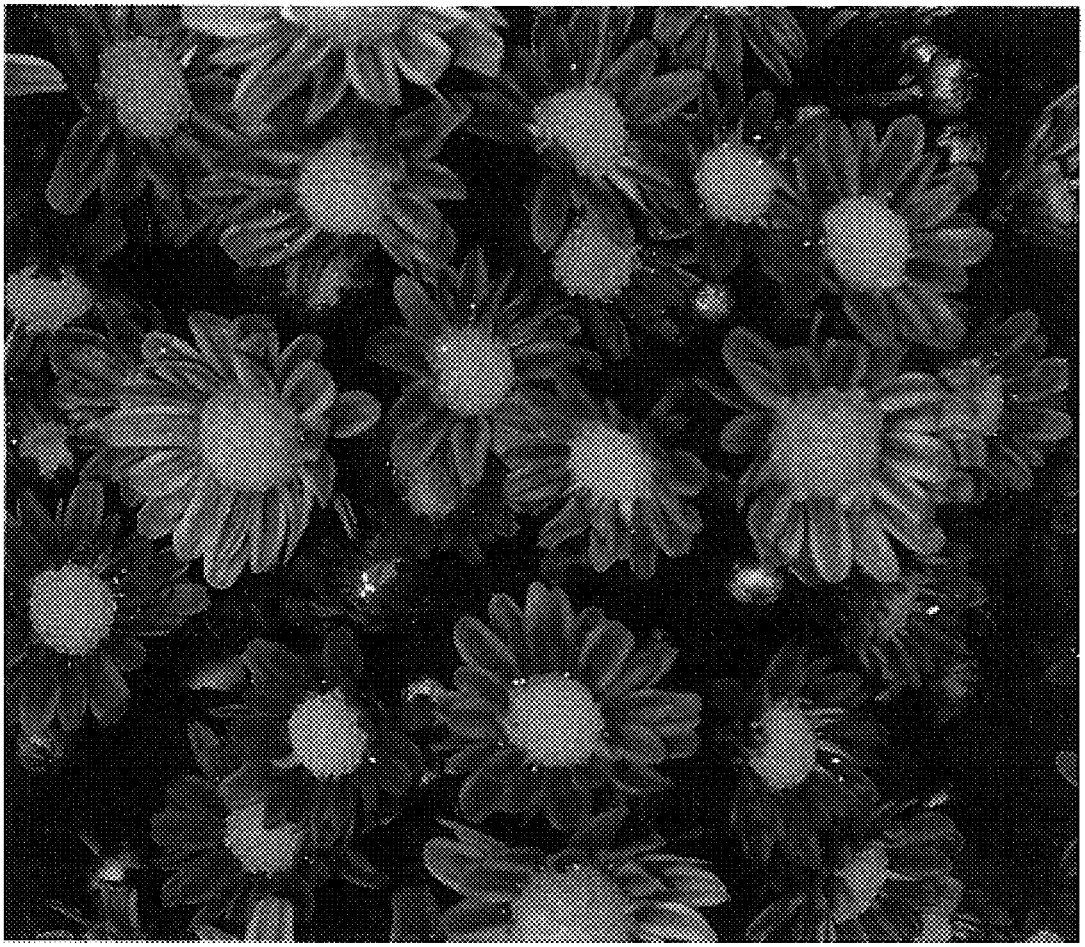

* * * * *